(12) United States Patent
Roy et al.

(10) Patent No.: US 11,802,783 B2
(45) Date of Patent: Oct. 31, 2023

(54) PASSIVE PRODUCTION LOGGING INSTRUMENT USING HEAT AND DISTRIBUTED ACOUSTIC SENSING

(71) Applicant: ConocoPhillips Company, Houston, TX (US)

(72) Inventors: Baishali Roy, Houston, TX (US); Kyle Friehauf, Houston, TX (US); Kevin T. Raterman, Houston, TX (US); Herbert W. Swan, Houston, TX (US); Jesse J. Constantine, Houston, TX (US); Ge Jin, Houston, TX (US)

(73) Assignee: ConocoPhillips Company, Houston, TX (US)

( * ) Notice: Subject to any disclaimer, the term of this patent is extended or adjusted under 35 U.S.C. 154(b) by 0 days.

(21) Appl. No.: 17/867,483

(22) Filed: Jul. 18, 2022

(65) Prior Publication Data
US 2023/0014753 A1 Jan. 19, 2023

Related U.S. Application Data (60) Provisional application No. 63/222,809, filed on Jul. 16, 2021.

(51) Int. Cl.
*G01F 1/684* (2006.01)
*G01N 33/28* (2006.01)
(Continued)

(52) U.S. Cl.
CPC .............. *G01F 1/684* (2013.01); *E21B 21/08* (2013.01); *G01N 29/024* (2013.01);
(Continued)

(58) Field of Classification Search
CPC .................................. G01F 1/684; E21B 21/08
See application file for complete search history.

(56) References Cited

U.S. PATENT DOCUMENTS

| 1,009,582 A | 11/1911 | Rottenthaler |
| 1,037,095 A | 8/1912 | Williams et al. |

(Continued)

FOREIGN PATENT DOCUMENTS

| GB | 2492802 A | 1/2013 |
| WO | WO-0148353 A1 | 7/2001 |

(Continued)

OTHER PUBLICATIONS

International Search Report and The Written Opinion of The International Searching Authority for International application No. PCT/US 22/37422 dated Oct. 6, 2022 (10 pages).

(Continued)

*Primary Examiner* — Kristina M Deherrera
*Assistant Examiner* — Jean F Morello
(74) *Attorney, Agent, or Firm* — Polsinelli PC (57) ABSTRACT

A system for measuring fluid flow in a wellbore is provided. A probe includes at least a heater. A fiber optic cable is connected to the probe. The system is programmed to perform operations including: changing an output of the heater to thereby change a temperature of drilling fluid moving over a fiber optic cable; measuring a strain on the fiber optic cable caused by changing the temperature of the drilling fluid; preliminarily determining a velocity of the drilling fluid from the measured strain; measuring at least a second parameter of the drilling fluid; adjusting the preliminary determined velocity based on the measured at least a second parameter to yield an adjusted velocity; and determining a flow rate of the drilling fluid based on the adjusted velocity.

20 Claims, 6 Drawing Sheets

(51) Int. Cl.
    *G01N 29/024*     (2006.01)
    *E21B 21/08*     (2006.01)

(52) U.S. Cl.
    CPC ..... *G01N 33/2823* (2013.01); *G01N 33/2847* (2013.01); *G01N 2291/011* (2013.01); *G01N 2291/0222* (2013.01)

(56) References Cited

U.S. PATENT DOCUMENTS

| | | |
|---|---|---|
| 1,045,822 A | 12/1912 | Dodge |
| 3,981,187 A | 9/1976 | Howell |
| 4,676,664 A | 6/1987 | Anderson et al. |
| 6,026,913 A | 2/2000 | Mandal et al. |
| 6,176,323 B1 | 1/2001 | Weirich et al. |
| 6,268,911 B1 | 7/2001 | Tubel et al. |
| 6,778,720 B1 | 8/2004 | Cekorich et al. |
| 7,055,604 B2 | 6/2006 | Jee et al. |
| 7,668,411 B2 | 2/2010 | Davies et al. |
| 8,505,625 B2 | 8/2013 | Ravi et al. |
| 8,630,816 B2 | 1/2014 | Park et al. |
| 8,646,968 B2 | 2/2014 | MacDougall et al. |
| 8,930,143 B2 | 1/2015 | Sierra et al. |
| 8,950,482 B2 | 2/2015 | Hill et al. |
| 9,116,119 B2 | 8/2015 | Le Floch |
| 9,273,548 B2 | 3/2016 | LeBlanc et al. |
| 9,347,310 B2 | 5/2016 | Unalmis et al. |
| 9,416,644 B2 | 8/2016 | McEwen-King et al. |
| 9,464,512 B2 | 10/2016 | Kalia et al. |
| 10,095,828 B2 | 10/2018 | Swan et al. |
| 2002/0180728 A1 | 12/2002 | Neff et al. |
| 2003/0205375 A1 | 11/2003 | Wright et al. |
| 2006/0010973 A1 | 1/2006 | Brown |
| 2006/0272809 A1 | 12/2006 | Tubel et al. |
| 2008/0277568 A1 | 11/2008 | Crickmore et al. |
| 2009/0114386 A1 | 5/2009 | Hartog et al. |
| 2009/0194333 A1 | 8/2009 | MacDonald |
| 2009/0326826 A1 | 12/2009 | Hull et al. |
| 2010/0076738 A1 | 3/2010 | Dean et al. |
| 2010/0200743 A1 | 8/2010 | Forster et al. |
| 2010/0200744 A1 | 8/2010 | Pearce et al. |
| 2010/0284250 A1 | 11/2010 | Cornish et al. |
| 2011/0019178 A1 | 1/2011 | Vlatas |
| 2011/0188347 A1 | 8/2011 | Thiercelin et al. |
| 2011/0288843 A1 | 11/2011 | Weng et al. |
| 2012/0017687 A1 | 1/2012 | Davis et al. |
| 2012/0057432 A1 | 3/2012 | Hill et al. |
| 2012/0067118 A1 | 3/2012 | Hartog et al. |
| 2012/0092960 A1 | 4/2012 | Gaston et al. |
| 2012/0133367 A1 | 5/2012 | Bittar et al. |
| 2012/0147924 A1 | 6/2012 | Hall |
| 2013/0023353 A1 | 1/2013 | Wright |
| 2013/0032338 A1 | 2/2013 | Kalia et al. |
| 2013/0204533 A1* | 8/2013 | Goodwin ............... G01K 17/06 702/9 |
| 2013/0211726 A1 | 8/2013 | Mestayer et al. |
| 2013/0298635 A1 | 11/2013 | Godfrey |
| 2013/0298665 A1 | 11/2013 | Minchau |
| 2013/0341008 A1 | 12/2013 | Brady et al. |
| 2014/0036628 A1 | 2/2014 | Hill et al. |
| 2014/0100274 A1 | 4/2014 | Bobotas et al. |
| 2014/0110124 A1 | 4/2014 | Goldner et al. |
| 2014/0126325 A1 | 5/2014 | Farhadiroushan et al. |
| 2014/0163889 A1 | 6/2014 | Finfer et al. |
| 2014/0180592 A1 | 6/2014 | Ravi et al. |
| 2014/0202240 A1 | 7/2014 | Skinner et al. |
| 2014/0216151 A1 | 8/2014 | Godfrey et al. |
| 2014/0246191 A1 | 9/2014 | Zolezzi-Garreton |
| 2014/0260588 A1 | 9/2014 | Jaaskelainen et al. |
| 2014/0290936 A1 | 10/2014 | Wills et al. |
| 2014/0358444 A1 | 12/2014 | Friehauf et al. |
| 2014/0365130 A1 | 12/2014 | Woods |
| 2015/0000932 A1 | 1/2015 | O'Brien |
| 2015/0014521 A1 | 1/2015 | Barfoot |
| 2015/0057934 A1 | 2/2015 | Ma et al. |
| 2015/0083405 A1 | 3/2015 | Dobroskok et al. |
| 2015/0135819 A1 | 5/2015 | Petrella et al. |
| 2015/0146759 A1 | 5/2015 | Johnston |
| 2015/0159478 A1 | 6/2015 | Georgi et al. |
| 2015/0331971 A1 | 11/2015 | Scollard et al. |
| 2016/0003032 A1 | 1/2016 | Grubb et al. |
| 2016/0138389 A1 | 5/2016 | Stokely |
| 2016/0146962 A1 | 5/2016 | Hayward |
| 2016/0191163 A1 | 6/2016 | Preston et al. |
| 2016/0265345 A1 | 9/2016 | In 'T Panhuis et al. |
| 2016/0266276 A1 | 9/2016 | Stokely et al. |
| 2016/0356125 A1 | 12/2016 | Bello et al. |
| 2017/0045410 A1 | 2/2017 | Crickmore et al. |
| 2017/0075005 A1 | 3/2017 | Ranjan et al. |
| 2017/0075006 A1 | 3/2017 | Dusterhoft et al. |
| 2017/0123103 A1 | 5/2017 | Tsakalakos et al. |
| 2017/0191363 A1 | 7/2017 | Dickenson |
| 2017/0205260 A1 | 7/2017 | Jaaskelainen et al. |
| 2017/0260839 A1 | 9/2017 | Beardmore et al. |
| 2017/0260842 A1 | 9/2017 | Jin et al. |
| 2017/0260846 A1 | 9/2017 | Jin et al. |
| 2017/0260849 A1 | 9/2017 | Friehauf et al. |
| 2017/0260854 A1 | 9/2017 | Jin et al. |
| 2017/0328181 A1 | 11/2017 | Kristjansson et al. |
| 2017/0342814 A1 | 11/2017 | Krueger et al. |
| 2018/0016890 A1 | 1/2018 | Friehauf |
| 2018/0045040 A1 | 2/2018 | Swan et al. |
| 2018/0217285 A1 | 8/2018 | Walters et al. |
| 2018/0230049 A1 | 8/2018 | Wysocki et al. |
| 2018/0348389 A1 | 12/2018 | Jaaskelainen et al. |
| 2019/0338621 A1 | 11/2019 | Jin et al. |

FOREIGN PATENT DOCUMENTS

| | | |
|---|---|---|
| WO | WO-2013092906 A2 | 6/2013 |
| WO | WO-2014201316 A1 | 12/2014 |
| WO | WO-2015065869 A1 | 5/2015 |
| WO | WO-2015076976 A1 | 5/2015 |
| WO | WO-2015094180 A1 | 6/2015 |
| WO | WO-2015107332 A1 | 7/2015 |
| WO | WO-2015153549 A1 | 10/2015 |
| WO | WO-2015170113 A1 | 11/2015 |
| WO | WO-2015187140 A1 | 12/2015 |
| WO | WO-2015187149 A1 | 12/2015 |
| WO | WO-2016007161 A1 | 1/2016 |
| WO | WO-2016069322 A1 | 5/2016 |
| WO | WO-2017027340 A1 | 2/2017 |
| WO | WO-2017039605 A1 | 3/2017 |
| WO | WO-2017156339 A1 | 9/2017 |
| WO | WO-2018204920 A1 | 11/2018 |

OTHER PUBLICATIONS

Awada A., et al., "Is That Interference? A Work Flow for Identifying and Analyzing Communication Through Hydraulic Fractures in a Multiwell Pad," SPE Journal, Oct. 2016, vol. 21(5), 13 Pages.

Becker M.W., et al., "Measuring Hydraulic Connection in Fractured Bedrock with Periodic Hydraulic Tests and Distributed Acoustic Sensing," Proceedings, 41st Workshop on Geothermal Reservoir Engineering. Stanford University, Stanford, California, Feb. 2016, 11 Pages.

Boman K., "DAS Technology Expands Fiberoptic Applications for Oil, Gas Industry," Rigzone Staff, May 4, 2015, 4 Pages.

Boone K., et al., "Monitoring Hydraulic Fracturing Operations Using Fiber-Optic Distributed Acoustic Sensing," Unconventional Resources Technology Conference, Jul. 2015, 8 Pages.

Bukhamsin A., et al., "Cointerpretation of Distributed Acoustic Temperature Sensing for Improved Smart Well Inflow Profiling," Society of Petroleum Engineers, May 23-26, 2016, 17 Pages.

Byrd R.H., et al., "A Limited-Memory Algorithm for Bound-Constrained Optimization," Department of Electrical Engineering and Computer Science, May 1994, vol. 16(5), 22 Pages.

Curtis M.R., et al., "Use of the Temperature Log for Determining Flow Rates in Producing Wells," Society of Petroleum Engineers of Aime, Sep. 30 to Oct. 3, 1973, 12 Pages.

Dakin J.P., et al., "Distributed Optical Fibre Raman Temperature Sensor Using a Semiconductor Light Source and Detector," Electronics Letters, Jun. 20, 1985, vol. 21(3), 2 Pages.

(56) References Cited

OTHER PUBLICATIONS

European Search Report issued in European Application No. EP17764137.0, dated Mar. 6, 2019, 4 Pages.
European Search Report issued in European Application No. EP17764143.8, dated Mar. 4, 2019, 4 Pages.
European Search Report issued in European Application No. EP17764146.1, dated Mar. 14, 2019, 4 Pages.
European Search Report issued in European Application No. EP17764150.3, dated Mar. 4, 2019, 5 Pages.
European Search Report issued in European Application No. EP17764151.1, dated Mar. 4, 2019, 4 Pages.
European Search Report issued in European Application No. EP18794756.9, dated Apr. 14, 2020, 4 Pages.
Glasbergen G., et al., "Real-Time Fluid Distribution Determination in Matrix Treatments Using DTS," Society of Petroleum Engineers, Feb. 2009, vol. 24(1), 12 Pages.
Grayson S., et al., "Monitoring Acid Stimulation Treaments in Naturally Fractured Reservoirs with Slickline Distributed Temperature Sensing," SPE International, Society of Petroleum Engineers, Mar. 24-25, 2015, 17 Pages.
Hesthammer J., et al., "From Seismic Data to Core Data: An Integrated Approach to Enhance Reservoir Characterization," Geological Society, London, Special Publications, Jan. 1, 2003, vol. 209, pp. 39-54.
Hoang D., et al., "A Novel Approach to Production Logging in Multiphase Horizontal Wells," Society of Petroleum Engineers, Sep. 28-29, 2004, 11 Pages.
Holley E.H., et a;,., "Interpreting Uncemented Multistage Hydraulic-Fracturing Completion Effectiveness by Use of Fiber-Optic DTS Injection Data," SPE Drilling & Completion, Sep. 2013, vol. 28(3), 11 Pages.
Holley E.H., et al., "Using Distributed Optical Sensing to Constrain Fracture Models and Confirm Reservoir Coverage in the Permian Basin," Society of Petroleum Engineers, Feb. 4-6, 2014, 14 Pages.
Horst J.V.T., et al., "Fiberoptic Sensing For Improved Wellbore Production Surveillance," International Petroleum Technology Conference, Jan. 20-22, 2014, 7 Pages.
International Search Report and the Written Opinion for International Application No. PCT/US2015/044286 dated Jul. 22, 2019, 10 Pages.
International Search Report and the Written Opinion for International Application No. PCT/US2017/021679 dated May 25, 2017, 8 Pages.
International Search Report and the Written Opinion for International Application No. PCT/US2017/021681 dated May 22, 2017, 11 Pages.
International Search Report and the Written Opinion for International Application No. PCT/US2018/031404 dated Jul. 13, 2018, 16 Pages.
International Search Report and the Written Opinion for International Application No. PCT/US2018/056327 dated Dec. 21, 2018, 12 Pages.
International Search Report and Written Opinion for International Application No. PCT/US2017/021659 dated Jun. 1, 2017, 8 Pages.
International Search Report and Written Opinion for International Application No. PCT/US2017/021667 dated Jun. 1, 2017, 9 Pages.
International Search Report and Written Opinion for International Application No. PCT/US2017/021670 dated May 25, 2017, 7 Pages.
International Search Report and Written Opinion for International Application No. PCT/US2017/021674 dated May 25, 2017, 11 Pages.
International Search Report and Written Opinion for International Application No. PCT/US2017/021678 dated Jun. 1, 2017, 8 Pages.
Jin G., et al., "Hydraulic-Fracture Geometry Characterization using Low-frequency DAS Signal," The Leading Edge, Dec. 2017, vol. 36(12), 6 Pages.
Johannessen K., et al., "Distributed Acoustic Sensing—A New Way of Listening to your Well/reservoir," SPE International, SPE 149602, Mar. 27-29, 2012, 9 Pages.
Lecalvez J.H., et al., "Real-Time Microseismic Monitoring of Hydraulic Fracture Treatment: A Tool to Improve Completion and Reservoir Management," Society of Petroleum Engineers, Jan. 29-31, 2007, 7 Pages.
Lord D.L., et al., "Study of Perforation Friction Pressure Employing a Large-Scale Fracturing Flow Simulator," Society of Petroleum Engineers, Sep. 25-28, 1994, 10 Pages.
McKinley R.M., et al., "Specialized Applications of Noise Logging," Society of Petroleum Engineers, Nov. 1, 1979, vol. 31(11), 9 Pages.
McKinley R.M., et al., "The Structure and Interpretation of Noise From Flow Behind Cemented Casing," Journal of Petroleum Technology, Mar. 1973, vol. 25(3), 10 Pages.
Molenaar M.M., et al., "Real-Time Downhole Monitoring of Hydraulic Fracturing Treatments Using Fibre Optic Distributed Temperature and Acoustic Sensing," Society of Petroleum Engineers, Mar. 20-22, 2012, 13 Pages.
Molenaar M.M., et al., "First Downhole Application of Distributed Acoustic Sensing for Hydraulic-Fracturing Monitoring and Diagnostics," SPE Drilling & Completion, Mar. 2012, 7 Pages.
Optasense, "Pipeline Integrity Management: Leak Detection," Retrieved from the Internet: URL: http://ace-control.com.sg/wp-content/uploads/2015/06/Pipeline-Integrity-Management-Leak-Detection.pdf, Retrieved on Jun. 10, 2019, 5 pages.
Ouyang L.B., et al., "Flow Profiling by Distributed Temperature Sensor (DTS) System—Expectation and Reality," Society of Petroleum Engineers, 2004, 14 Pages.
Ouyang L.B., et al., "Flow Profiling by Distributed Temperature Sensor (DTS) System—Expectation and Reality," Society of Petroleum Engineers, May 2006, vol. 21(2), 14 Pages.
Paleja R., et al., "Velocity Tracking for Flow Monitoring and Production Profiling Using Distributed Acoustic Sensing," Society of Petroleum Engineers, Sep. 28-30, 2015, 16 Pages.
Portis D.H., et al., "Searching for the Optimal Well Spacing in the Eagle Ford Shale: A Practical Tool-Kit," Unconventional Resources Technology Conferences, Aug. 12-14, 2013, 8 Pages.
Ramey H.J., et al., "Wellbore Heat Transmission," Society of Petroleum Engineers, Apr. 1962, 9 Pages.
Raterman K.T., et al., "Sampling a Stimulated Rock Volume: An Eagle for Example," Applied Geoscience Conference, Jul. 2017, 26 Pages.
Rector J.W., et al., "The Use of an Active Drill Bit for Inverse VSP Measurements," Exploration Geophysics, Dec. 6, 2018, 5 Pages.
Ribeiro et al., "Detecting Fracture Growth Out of Zone Using Temperature Analysis," Oct. 27-29, 2014, SPE-1707 46 MS, SPE Annual Technical Conference and Exhibition, Amsterdam, The Netherlands, pp. 1263-1278, (Year: 2014).
Sellwood S.M., et al., "An In-well Heat-tracer-test Method for Evaluating Borehole Flow Conditions," Springer-Verlag Berlin Heidelberg, Aug. 29, 2015, 14 Pages.
Sierra J., et al., "DTS Monitoring Data of Hydraulic Fracturing: Experiences and Lessons Learned," Society of Petroleum Engineers, 2008, 15 Pages.
SPE-107854-MS (2007)Tardy, et al., "An Experimentally Validated Wormhole Model for Self-Diverting and Conventional Acids in Carbonate Rocks Under Radial Flow Conditions", Society of Petroleum Engineers, 2007, 17 pages.
Webster P., et al., "Developments in Diagnostic Tools for Hydraulic Fracture Geometry Analysis," Unconventional Resources Technology Conference, Aug. 12-14, 2013, 7 Pages.
Webster P., et al., "Micro-Seismic Detection using Distributed Acoustic Sensing," SEG Houston 2013 Annual Meeting, Aug. 12-14, 2013, 5 Pages.
Wheaton B., et al., "A Case Study of Completion Effectiveness in the Eagle Ford Shale Using DAS/DTS Observations and Hydraulic Fracture Modeling," Society of Petroleum Engineers, Feb. 9-11, 2016, 11 Pages.
Wu K., et al., "Mechanism Analysis of Well Interference in Unconventional Reservoirs: Insights From Fracture-Geometry Simulation Between Two Horizontal Wells," Society of Petroleum Engineers, Feb. 23, 2017, 9 Pages.

* cited by examiner

PASSIVE PRODUCTION LOGGING INSTRUMENT USING HEAT AND DISTRIBUTED ACOUSTIC SENSING

CROSS-REFERENCE TO RELATED APPLICATION

The present application claims priority to U.S. Patent Application No. 63/222,809, entitled "Passive Production Logging Instrument Using Heat and Distributed Acoustic Sensing" and filed on Jul. 16, 2021, which is specifically incorporated by reference in its entirety herein.

FIELD

Various implementations described herein generally relate to well logging techniques used in oil and gas recovery operations. More specifically, various implementations passive sensors with applied heat and sound to calculate the rate of fluid flow moving through a wellbore.

BACKGROUND

It has become common in oil, gas, and other similar weds to utilize well logging surveys to determine the fraction (relative amounts) of oil, gas and unwanted water present in the production zone. This data, along with measurements of the fluid flow velocity, porosity, cross-section of the well, pressure, and temperature, may be used to determine production rates and other information from each zone of interest in the well. Such data is useful for optimizing the well's production, oil recovery, water shut-off and/or fracturing sequence, to achieve better reservoir management and reduce intervention costs. A well log can also be used to identify inefficiency with the well or optimize well and asset management decisions.

Well logging surveys are performed using logging tools that generally comprise at least one sensor and measure at least one parameter. Logging tools have included spinner type flow meters with attached temperature sensors, which rotate when immersed within a flow of drilling fluid. However, this type of logging tool has difficulties with mechanical effectiveness. For example, the impeller of the spinner operates on a bearing, which wears and requires frequent inspection and replacement to keep frictional effects from influencing the measurements. Another disadvantage, which increases logging time on the well, is that calibration must be done downhole by making several extra logging runs at various logging speeds. Additionally, the tool requires borehole cleanup before the survey to prevent sensor damage, significantly increasing the cost. Finally, the measurements are less reliable in horizontal wells due to fluid segregation.

Fiber-optic sensing technology has recently been deployed in the oil industry. Compared with electronic-based sensing tools, fiber-optic sensing has many advantages. First, all the sensing instruments are at the surface, so there is no power supply, moving parts, or electronics required in the borehole. Also, fiber-optic sensing can provide measurements along the entire fiber length (as long as 10 miles) with a spatial resolution in terms of feet. Thus, it can cover the entire wellbore simultaneously without having to move the tools. Finally, the diameter of the sensing fibers is usually in the range of millimeters, which can be easily integrated into the existing wireline, coil tubing, or carbon-rod cables, and they can be easily protected to endure harsh borehole environments.

Optical fibers have thus been used in a variety of logging tools. One technique is Distributed Acoustic Sensing ("DAS") that employs a measure of Rayleigh scatter distributed along the fiber optic cable. A coherent laser pulse from an interrogator is sent along the optic fiber, and scattering sites within the fiber itself causes the fiber to act as a distributed interferometer with a pre-set gauge length. Thus, interactions between the light and material of the fiber can cause a small amount of light to backscatter and return to the input end, where it is detected and analyzed. Acoustic waves, when interacting with the materials that comprise the optic fiber, create small dynamic density changes, thus affecting the refractive index of the fiber optic cable. These changes affect the backscatter characteristics, thus becoming detectable events. Using time-domain techniques, event location is precisely determined, providing fully distributed sensing within one meter or less resolution.

What is needed in the art are improved methods of well logging for all aspects of oil and gas production. Although well logging is already quite successful, even incremental improvements in technology can mean the difference between cost-effective production and reserves that are uneconomical to produce. Ideally, the improved methods would have high spatial and temporal resolution while retaining the ability to provide real-time "snap shots" of the production zone's fluid allocation.

SUMMARY

According to one implementation, a method for measuring fluid flow in a wellbore is provided. The method includes: deploying a probe into the wellbore, the probe including at least a heater, the probe being connected to monitoring equipment by a fiber optic cable; changing an output of the heater to thereby change a temperature of drilling fluid moving over a fiber optic cable; first measuring a strain on the fiber optic cable caused by changing the temperature of the drilling fluid; preliminarily determining a velocity of the drilling fluid from the measured strain; second measuring at least a second parameter of the drilling fluid; adjusting the preliminary determined velocity based on the measured at least a second parameter to yield an adjusted velocity; and determining a flow rate of the drilling fluid based on the adjusted velocity.

The above implementation may have various optional features. The changing a heater output may be heating the drilling fluid, which may itself be turning on the heater. The changing a heater output may be turning off the heater. The at least a second parameter may include a speed of sound through the drilling fluid and/or a hydrostatic head of fluid in the wellbore. For speed of sound, the adjusting may include determining approximate relative amounts of water and oil in the drilling fluid from the measured speed of sound through the drilling fluid and compensating for influence of the determined approximate relative amounts of water and oil on the preliminary determined velocity. For a hydrostatic head, the adjusting may include determining the hydrostatic head of drilling fluid in the wellbore and compensating for influence of the determined hydrostatic head on the preliminary determined velocity.

According to another implementation, a system for measuring fluid flow in a wellbore is provided. A probe includes at least a heater. A fiber optic cable is connected to the probe. The system is programmed to perform operations including: changing an output of the heater to thereby change a temperature of drilling fluid moving over a fiber optic cable; measuring a strain on the fiber optic cable caused by changing the temperature of the drilling fluid; preliminarily determining a velocity of the drilling fluid from the measured strain; measuring at least a second parameter of the drilling fluid; adjusting the preliminary determined velocity based on the measured at least a second parameter to yield an adjusted velocity; and determining a flow rate of the drilling fluid based on the adjusted velocity.

The above implementation may have various optional features. The above implementation may have various optional features. The changing a heater output may be heating the drilling fluid, which may itself be turning on the heater. The changing a heater output may be turning off the heater. The at least a second parameter may include a speed of sound through the drilling fluid and/or a hydrostatic head of fluid in the wellbore. For speed of sound, the adjusting may include determining approximate relative amounts of water and oil in the drilling fluid from the measured speed of sound through the drilling fluid and compensating for influence of the determined approximate relative amounts of water and oil on the preliminary determined velocity. For a hydrostatic head, the adjusting may include determining the hydrostatic head of drilling fluid in the wellbore and compensating for influence of the determined hydrostatic head on the preliminary determined velocity.

The foregoing is intended to be illustrative and is not meant in a limiting sense. Many features of the implementations may be employed with or without reference to other features of any of the implementations. Additional aspects, advantages, and/or utilities of the presently disclosed technology will be set forth in part in the description that follows and, in part, will be apparent from the description, or may be learned by practice of the presently disclosed technology.

BRIEF DESCRIPTION OF THE DRAWINGS

In order to describe the manner in which the above-recited and other advantages and features of the disclosure can be obtained, a more particular description of the principles briefly described above will be rendered by reference to specific example implementations thereof which are illustrated in the appended drawings. Understanding that these drawings depict only exemplary implementations of the disclosure and are not therefore to be considered to be limiting of its scope, the principles herein are described and explained with additional specificity and detail through the use of the accompanying drawings in which.

DETAILED DESCRIPTION

In the following description, various implementations will be illustrated by way of example and not by way of limitation in the figures of the accompanying drawings. References to various implementations in this disclosure are not necessarily to the same implementation, and such references mean at least one. While specific implementations and other details are discussed, it is to be understood that this is done for illustrative purposes only. A person skilled in the relevant art will recognize that other components and configurations may be used without departing from the scope and spirit of the claimed subject matter.

Specific details are provided in the following description to provide a thorough understanding of implementations. However, it will be understood by one of ordinary skill in the art that implementations may be practiced without these specific details. For example, systems may be shown in block diagrams so as not to obscure the implementations in unnecessary detail. In other instances, well-known processes, structures and techniques may be shown without unnecessary detail in order to avoid obscuring example implementations.

References to one or an implementation in the present disclosure can be, but not necessarily are, references to the same implementation; and such references mean at least one of the implementations.

References to any "example" herein (e.g., "for example", "an example of", by way of example" or the like) are to be considered non-limiting examples regardless of whether expressly stated or not.

Reference to "one implementation" or "an implementation" means that a particular feature, structure, or characteristic described in connection with the implementation is included in at least one implementation of the disclosure. The appearances of the phrase "in one implementation" in various places in the specification are not necessarily all referring to the same implementation, nor are separate or alternative implementations mutually exclusive of other implementations. Moreover, various features are described which may be exhibited by some implementations and not by others. Similarly, various features are described which may be features for some implementations but not other implementations.

The terms used in this specification generally have their ordinary meanings in the art, within the context of the disclosure, and in the specific context where each term is used. Alternative language and synonyms may be used for any one or more of the terms discussed herein, and no special significance should be placed upon whether or not a term is elaborated or discussed herein. Synonyms for certain terms are provided. A recital of one or more synonyms does not exclude the use of other synonyms. The use of examples anywhere in this specification including examples of any terms discussed herein is illustrative only and is not intended to further limit the scope and meaning of the disclosure or of any exemplified term. Likewise, the disclosure is not limited to various implementations given in this specification.

Without intent to limit the scope of the disclosure, examples of instruments, apparatus, methods and their related results according to the implementations of the present disclosure are given below. Note that titles or subtitles may be used in the examples for convenience of a reader, which in no way should limit the scope of the disclosure. Unless otherwise defined, technical and scientific terms used herein have the meaning as commonly understood by one of ordinary skill in the art to which this disclosure pertains. In the case of conflict, the present document, including definitions will control.

Several definitions that apply throughout this disclosure will now be presented. The term "substantially" is defined to be essentially conforming to the particular dimension, shape, or other feature that the term modifies, such that the component need not be exact. For example, "substantially cylindrical" means that the object resembles a cylinder but can have one or more deviations from a true cylinder. The term "comprising" when utilized means "including, but not necessarily limited to"; it specifically indicates open-ended inclusion or membership in the so-described combination, group, series and the like. The term "a" means "one or more" unless the context clearly indicates a single element. The term "about" when used in connection with a numerical value means a variation consistent with the range of error in equipment used to measure the values, for which ±5% may be expected. "First," "second," etc., re labels to distinguish components or blocks of otherwise similar names but does not imply any sequence or numerical limitation. When an element is referred to as being "connected," or "coupled," to another element, it can be directly connected or coupled to the other element or intervening elements may be present. And/or" for two possibilities means either or both of the stated possibilities, and when present with three or more stated possibilities means any individual possibility alone, all possibilities collectively, or some combination of possibilities that is less than all of the possibilities. The language in the format "at least one of A, . . . and N" where A through N are possibilities means "and/or" for the stated possibilities.

By contrast, when an element is referred to as being "directly connected," or "directly coupled," to another element, there are no intervening elements present. Other words used to describe the relationship between elements should be interpreted in a like fashion (e.g., "between," versus "directly between," "adjacent," versus "directly adjacent," etc.).

As used herein, the term "front", "rear", "left," "right," "top" and "bottom" or other terms of direction, orientation, and/or relative position are used for explanation and convenience to refer to certain features of this disclosure. However, these terms are not absolute, and should not be construed as limiting this disclosure.

All temperatures herein are in Celsius unless otherwise specified.

Shapes as described herein are not considered absolute. As is known in the art, surfaces often have waves, protrusions, holes, recesses, etc. to provide rigidity, strength and functionality. All recitations of shape (e.g., cylindrical) herein are to be considered modified by "substantially" regardless of whether expressly stated in the disclosure or claims, and specifically accounts for variations in the art as noted above.

It should also be noted that in some alternative implementations, the functions/acts noted may occur out of the order noted in the figures. For example, two steps disclosed or shown in succession may in fact be executed substantially concurrently or may sometimes be executed in the reverse order, depending upon the functionality/acts involved.

General Architecture

Figure 1:
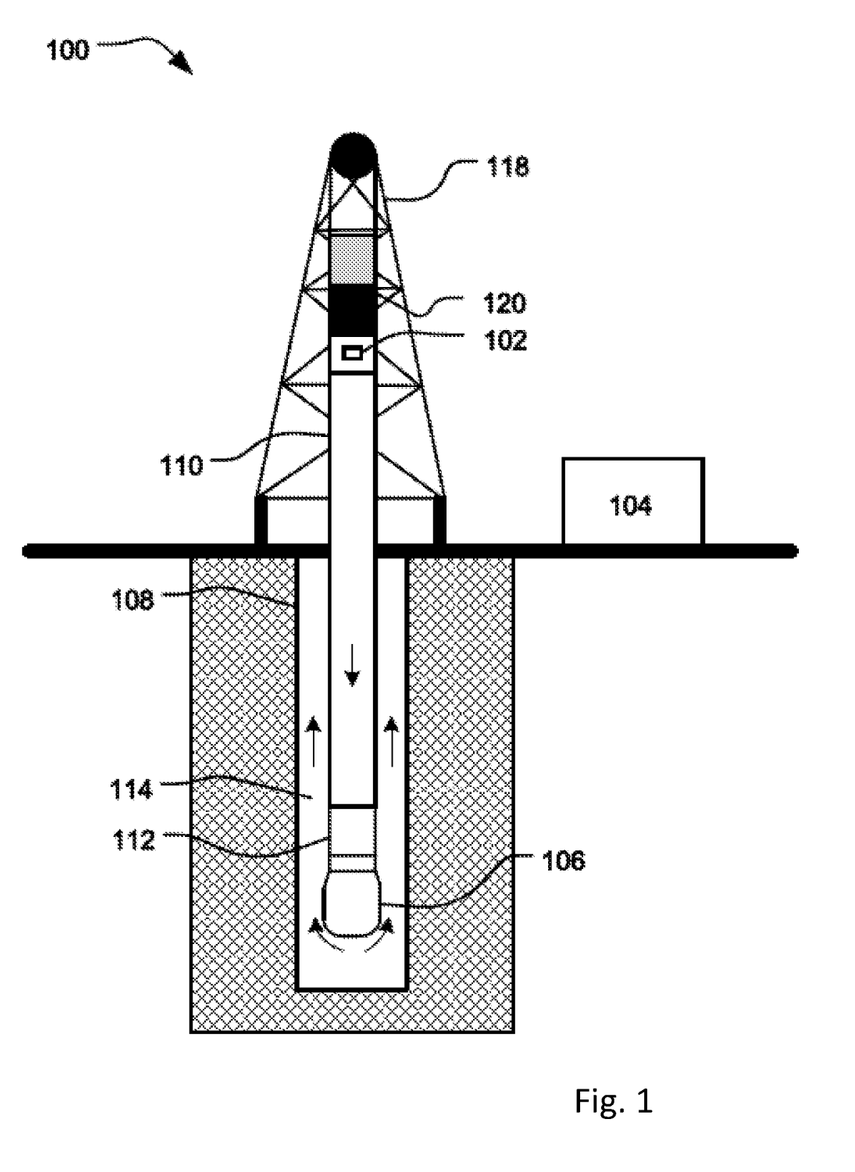
FIG. 1 shows a general architecture of a wellbore and associated drilling equipment.
Figure 2:
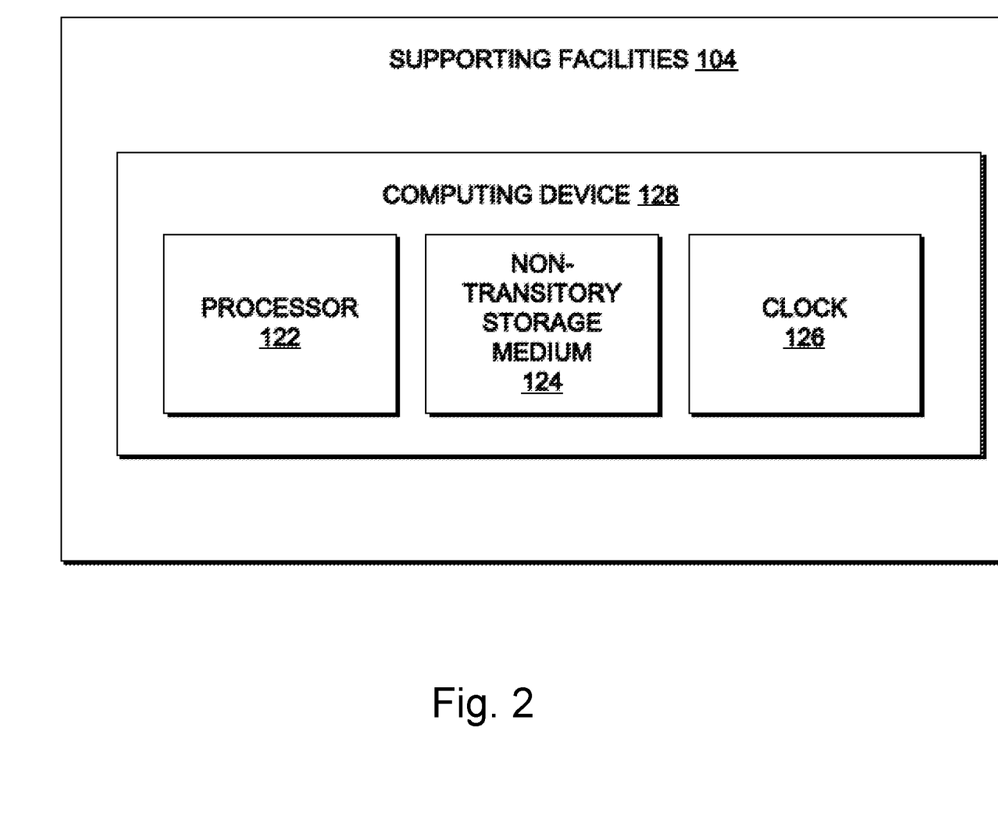
FIG. 2 shows a general architecture of computer equipment used by implementations herein.

Turning to FIGS. 1 and 2, an example drilling system 100 is illustrated in use with a drilling rig 118 having a top drive motor 120 at a surface of a wellbore 108. The drilling rig 118 includes a drill string 110 extending into the wellbore 108 with one or more surface sensors 102 and supporting facilities 104 positioned at a top of the wellbore 108. The wellbore 108 extends into the ground and is formed via a drilling operation using the drill string 110. A depth of the wellbore 108 can range from a few feet to over a mile into the ground and can extend in one or more directions. The drill string 110 includes a drill pipe and a bottom hole assembly (BHA) 112 positioned at a bottom of the drill string 110. The BHA 112 can include a plurality of components. In the exemplary implementation, the BHA 112 includes a steering unit, a mud motor, a drill motor, a drill collar, and a drill bit 106. It is foreseen that the BHA 112 may include fewer or additional components. The drill string 110 extends into the wellbore 108 so that the drill bit 106 of the BHA 112 is in contact with a geological formation to crush and/or scrape the geological formation, thereby increasing a length of the wellbore 108 in a downward direction, a lateral direction, and/or any other suitable direction. In the exemplary implementation, the drill bit 106 is driven by the top drive motor 120 and/or the mud motor positioned near the drill bit 106. It is foreseen, however, that the drilling rig 118 may use a kelly drive or a rotary table to drive the drill bit 106.

A drilling fluid 114 can be continuously circulated within the wellbore 108 via a pump to facilitate operation of the BHA 112, e.g., drilling. The drilling fluid 114 can be introduced into the drill string 110 via an opening of the drill string 110 and pumped down the drill string 110 via the pump. The drilling fluid 114 exits the drill string 110 through the drill bit 106 and circulates upwards through an annulus of the wellbore 108. The drilling fluid 114 has multiple functions including, but not limited to, cooling the drill bit 106, lubricating the drill bit 106, and/or transporting debris generated by the drill bit 106 away from the drill bit 106, e.g., up the annulus of the wellbore 108 and to the surface of the wellbore 108. The drilling fluid 114 may be water, oil, a synthetic based composition, gas, or a combination thereof, and may include one or more additives and/or particles.

Each of the one or more surface sensors 102 are configured to measure drilling data, for example, a surface torque of the drill string 110 may yield a data stream of the drill string torque. It is foreseen that the surface sensors 102 may be configured to measure vibration, weight on bit (WOB), lateral acceleration, rotations per minute (RPM), tension, flow rate, temperature, pressure, or any other suitable data related to the drill string 110 during drilling that can be measured from the surface. It is foreseen that the one or more surface sensors 102 may be, or include, a strain gauge, accelerometer, gyroscope, and/or seismometer. It is foreseen that the one or more surface sensors 102 may be configured to measure same or different data relative to each other.

In the exemplary implementation, the one or more surface sensors 102 are positioned on the drill string 110, at or adjacent to the top of the drill string 110 at the surface of the wellbore 108, but it is foreseen that the one or more surface sensors 102 can be positioned along any portion of the drill string 110 proximate to or above the surface of the wellbore 108. For instance, it is foreseen that the one or more surface sensors 102 can be in a sub positioned under the top drive motor 120 and above the drill string 110.

The supporting facilities 104, as illustrated in FIG. 2, include a computing device 128. The computing device 128 includes a processor 122 and a non-transitory storage medium 124 (e.g., hardware memory). The computing device 128 is configured to communicate with the surface sensors 102. In the exemplary implementation, the drilling data is transmitted from the surface sensors 102 to the non-transitory storage medium 124 via a wireless connection of a wireless network, although it is foreseen that the drilling data can be transmitted continuously to the non-transitory storage medium 124 via a wired connection, for example a wire and/or optic fiber.

Passive Probe

Figure 3:
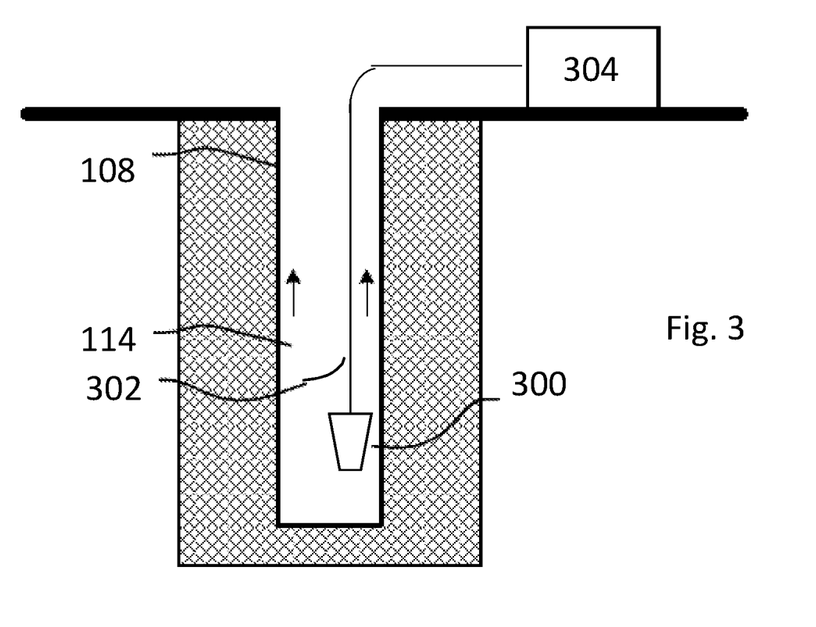
FIG. 3 shows an implementation of a probe deployed down a wellbore.
Figure 4:
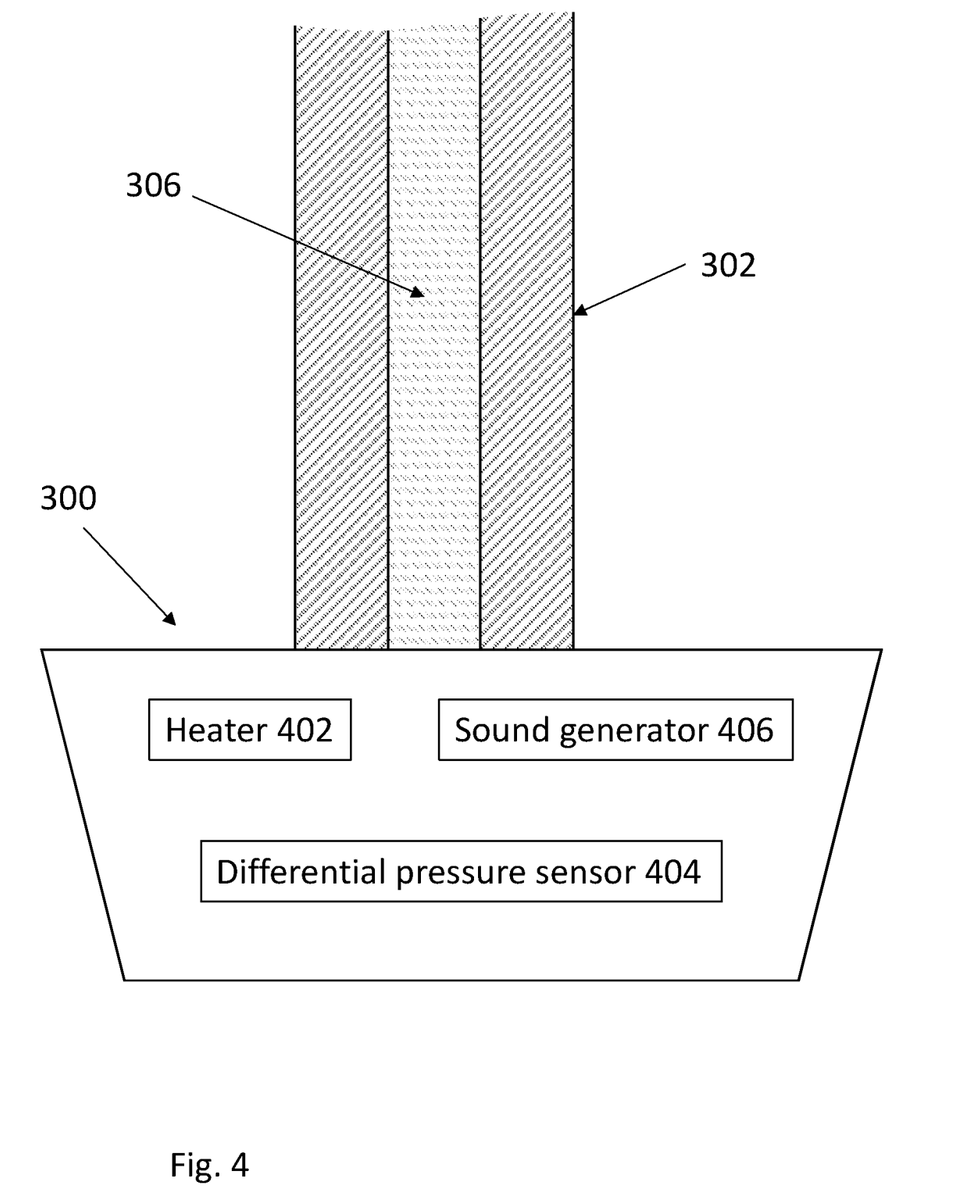
FIG. 4 shows an implementation of the internal components of a probe.

Referring now to FIGS. 3 and 4, an implementation of a probe 300 is shown. Probe 300 is mounted on the far end of a tool string 302 that connects to a DAS acquisition unit 304 on the surface. Tool string 302 may be conventional wireline, carbon rod or coiled tubing or the like with embedded laser supported fiber optic cable 306 and other electrical cabling as is known in the art. Tool string 302 may be stored and lowered by a drum (not shown) or other similar methodology into the flow stream of wellbore 108 to the desired depth as is known in the art and not further discussed herein. DAS acquisition unit may be part of surface sensors 102 and/or supporting facilities 104, a standalone unit, or a combination thereof. The presently disclosed technology is not limited to the particulars of the tool string or the components that receive and process data therefrom.

Probe 300 includes a heater 402, a differential pressure sensor 404, and a sound generator 406. These probe components may before part of a single unit as probe 300, the probe components of probe 300 may be dispersed in different structures, and/or the like. Control over the probe components may lie in the components themselves, surface sensors 102, supporting facilities 104, DAS acquisition unit 304, other components, or combinations thereof.

Figure 5:
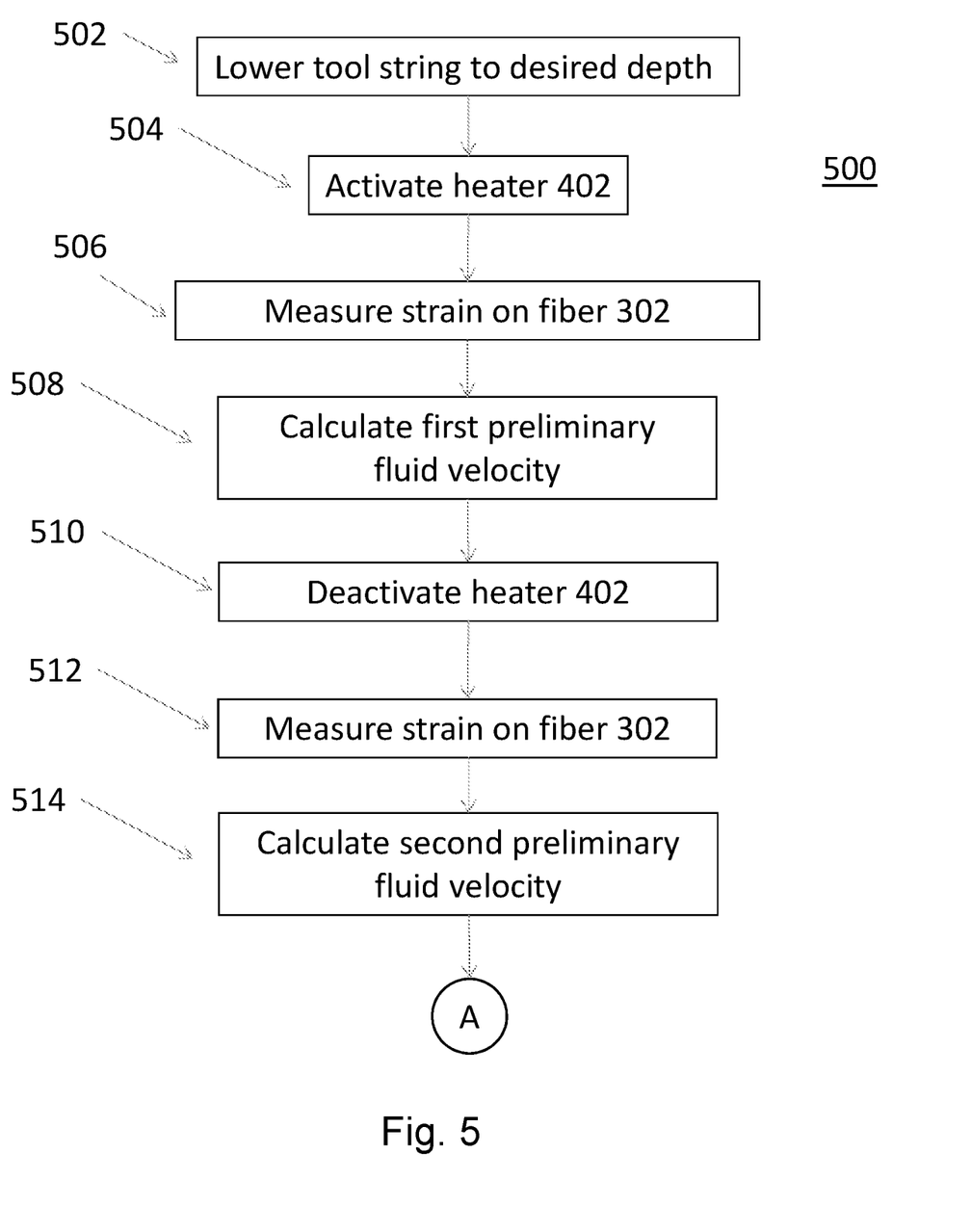
FIGS. 5 and 6 are a flowchart of an implementation for using a probe to measure flow rate of drilling fluid flow in a wellbore.

Referring now to FIG. 5, a flowchart 500 is shown for utilizing probe 300 to determine a flow rate of fluid from wellbore 108. The overall goal of the methodology of flowchart 500 is to determine with a fair degree of accuracy the flow rate of the drilling fluid 114 emerging from wellbore 108. Flow rate can then be determined based on the velocity of the drilling fluid and the size of the opening that the drilling fluid 114 emerges from (e.g., the cross-section of wellbore 108 minus the cross-section of any components inserted in wellbore 108).

At step 502, tool string 302 is lowered into the wellbore 108 to place probe 300 at the desired depth. Ambient temperature drilling fluid 114 will move along tool string 302 and create a baseline strain on fiber optic cable 306.

At step 504, heater 402 is activated, heating the drilling fluid 114 flowing over probe 300 as drilling fluid 114 moves up wellbore 108 toward the surface. The sudden addition of heat creates transition point in the drilling fluid 114 with ambient temperature drilling fluid 114 above the transition point and heated drilling fluid 114 below the transition point. As drilling fluid 114 moves toward the surface, the higher temperature drilling fluid 114 creates a different strain on fiber optic cable 306 relative to the ambient temperature drilling fluid 114. The movement of the transition point along fiber optic cable 306 thus forms a leading edge of a change in strain on fiber optic cable. At step 506, DAS acquisition unit 304 identifies this strain change as drilling fluid 114 moves along fiber optic cable 306 in a manner as is known in the art. At step 508, a first preliminary velocity of the drilling fluid 114 is calculated from the movement of the detected strain change (e.g., the distance that the strain change traveled along fiber optic cable 306 relative to the amount of time to travel that distance).

At step 510, heater 402 is deactivated, such that the previously heated drilling fluid 114 is pushed up wellbore 108 toward the surface by fresh flowing ambient (unheated) temperature drilling fluid 114. Flow of previously heated drilling fluid 114 followed by the ambient temperature drilling fluid 114 creates a trailing edge of applied strain change on the fiber optic cable 306 within tool string 302. At step 512, DAS acquisition unit 304 measures this strain in a manner as is known in the art. At step 514, a second preliminary velocity of the fluid flow is calculated from the detected strain in the same manner as discussed above.

In theory, the methodology could use the first and/or second preliminary velocities to calculate the fluid flow rate based on velocity and the size of the opening of the fluid pathway (e.g., the cross-section area of the wellbore opening minus the area of any inserted components, such as tool string 302). However, measuring velocities directly from strain on fiber optic cable 306 carries a degree of inaccuracy (and thus the designation as "preliminary") due to the influence of other characteristics of the fluid flow. Accuracy in calculating of velocity and/or fluid flow rate can be improved by measuring other characteristics of the fluid flow.

One such characteristic is the "holdup" of the fluid flow—the amount of water in drilling fluid 114 relative to the amount of oil. Holdup can be estimated based on the speed of sound passing through drilling fluid. For example, if the fluid was completely water then the speed would be that of sound through water (1480 feet per second), and if the fluid completely oil then the speed would be that of sound through petroleum oil (1330 feet per second). If the fluid is a combination of oil and water, then the speed of sound through the fluid will be somewhere between the two extremes, and the holdup can be calculated from the speed of sound through the fluid in a manner known in the art.

Figure 6:
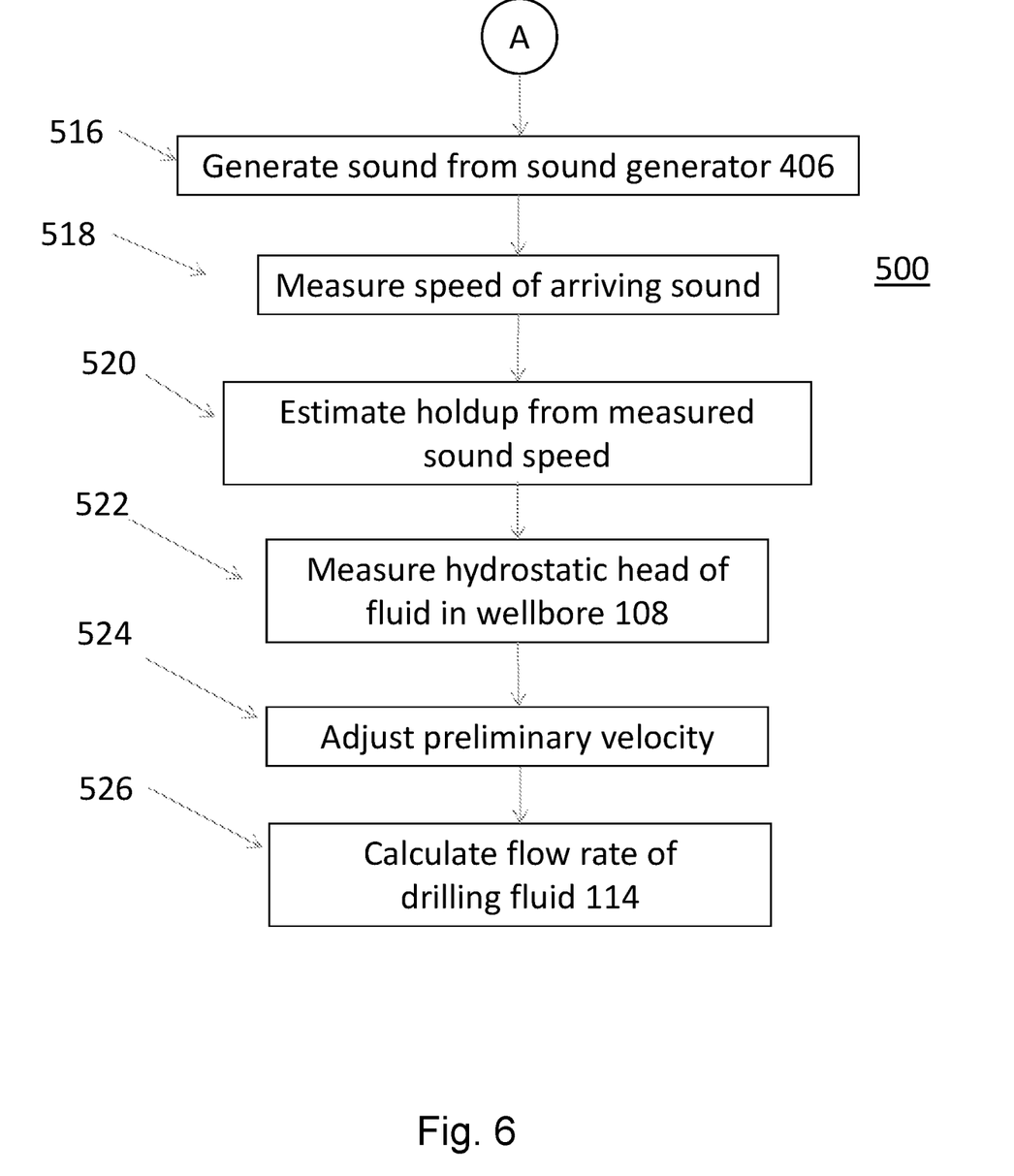

To measure holdup, at step 516 sound generator 406 generates a sound that perpetuates through the drilling fluid 114 up to the top of the wellbore. The sound wave induces a corresponding vibration in fiber optic cable 306. At step 518 DAS 304 analyzes the output of the fiber optic cable 306 as influenced by the vibration to determine characteristic of the applied sound. At step 520, the holdup is estimated based on the measured characteristics from step 518 as is known in the art.

Another characteristic that can improve the velocity measurement is the hydrostatic head of the fluid within wellbore 108. At step 522, differential pressure sensor 404 measures the hydrostatic head of the fluid in a manner as is known in the art.

At step 524, the results of the measurements for holdup and/or hydrostatic head are used to adjust the first and/or second primary velocity measurements to a (theoretically) more accurate value as an adjusted velocity. Once the adjusted velocity is calculated, flow rate is calculated at step 526 from the adjusted velocity and the size of the opening through which the fluid flows.

The above implementations provide a passive sensor approach to measuring flow rate in a wellbore. The use of fiber optic cables provides the sensors and information needed to assess flow rate without the need for complex mechanical systems that are susceptible to temperature, damage, and debris.

General Computer Architecture

Various implementations discussed or suggested herein can be implemented in a wide variety of operating environments, which in some cases can include one or more user computers, computing devices, or processing devices which can be used to operate any of a number of applications. User or client devices can include any of a number of general purpose individual computers, such as desktop or laptop computers running a standard operating system, as well as cellular, wireless, and handheld devices running mobile software and capable of supporting a number of networking and messaging protocols. Such a system also can include a number of workstations running any of a variety of commercially-available operating systems and other known applications for purposes such as development and database management. These devices also can include other electronic devices, such as dummy terminals, thin-clients, gaming systems, and other devices capable of communicating via a network.

Most implementations utilize at least one network that would be familiar to those skilled in the art for supporting communications using any of a variety of commercially available protocols, such as TCP/IP, OSI, FTP, UPnP, NFS, CIFS, and AppleTalk. The network can be, for example, a local area network, a wide-area network, a virtual private network, the Internet, an intranet, an extranet, a public switched telephone network, an infrared network, a wireless network, and any combination thereof.

In implementations where the computing device includes a Web server, the Web server can run any of a variety of server or mid-tier applications, including HTTP servers, FTP servers, CGI servers, data servers, Java servers, and business application servers. The server(s) also may be capable of executing programs or scripts in response requests from user devices, such as by executing one or more Web applications that may be implemented as one or more scripts or programs written in any programming language, such as Java®, C, C# or C++, or any scripting language, such as Perl, Python, or TCL, as well as combinations thereof. The server(s) may also include database servers, including without limitation those commercially available from Oracle®, Microsoft®, Sybase®, and IBM®.

The environment can include a variety of data stores and other memory and storage media as discussed above. These can reside in a variety of locations, such as on a storage medium local to (and/or resident in) one or more of the computers or remote from any or all of the computers across the network. In a particular set of implementations, the information may reside in a storage-area network ("SAN") familiar to those skilled in the art. Similarly, any necessary files for performing the functions attributed to the computers, servers, or other network devices may be stored locally and/or remotely, as appropriate. Where a system includes computerized devices, each such device can include hardware elements that may be electrically coupled via a bus, the elements including, for example, at least one central processing unit (CPU), at least one input device (e.g., a mouse, keyboard, controller, touch screen, or keypad), and at least one output device (e.g., a display device, printer, or speaker). Such a system may also include one or more storage devices, such as disk drives, optic storage devices, and solid-state storage devices such as random-access memory ("RAM") or read-only memory ("ROM"), as well as removable media devices, memory cards, flash cards, etc.

Such devices also can include a computer-readable storage media reader, a communications device (e.g., a modem, a network card (wireless or wired), an infrared communication device, etc.), and working memory as described above. The computer-readable storage media reader can be connected with, or configured to receive, a computer-readable storage medium, representing remote, local, fixed, and/or removable storage devices as well as storage media for temporarily and/or more permanently containing, storing, transmitting, and retrieving computer-readable information. The system and various devices also typically will include a number of software applications, modules, services, or other elements located within at least one working memory device, including an operating system and application programs, such as a client application or Web browser. It should be appreciated that alternate implementations may have numerous variations from that described above. For example, customized hardware might also be used and/or particular elements might be implemented in hardware, software (including portable software, such as applets), or both. Further, connection to other computing devices such as network input/output devices may be employed.

Storage media and computer readable media for containing code, or portions of code, can include any appropriate media known or used in the art, including storage media and communication media, such as but not limited to volatile and non-volatile, removable and non-removable media implemented in any method or technology for storage and/or transmission of information such as computer readable instructions, data structures, program modules, or other data, including RAM, ROM, EEPROM, flash memory or other memory technology, CD-ROM, digital versatile disk (DVD) or other optic storage, magnetic cassettes, magnetic tape, magnetic disk storage or other magnetic storage devices, or any other medium which can be used to store the desired information and which can be accessed by a system device. Based on the disclosure and teachings provided herein, an individual of ordinary skill in the art will appreciate other ways and/or methods to implement the various implementations.

The specification and drawings are to be regarded in an illustrative rather than a restrictive sense. It will, however, be evident that various modifications and changes may be made thereunto without departing from the broader spirit and scope as set forth in the claims.

What is claimed is:

1. A method to measure fluid flow in a wellbore, the method comprising:
   deploying a probe into the wellbore, the probe including at least a heater, the probe being connected to monitoring equipment by a fiber optic cable;
   changing an output of the heater to thereby change a temperature of drilling fluid moving over the fiber optic cable;
   first measuring a strain on the fiber optic cable caused by changing the temperature of the drilling fluid to yield a measured strain;
   preliminarily determining a velocity of the drilling fluid from the measured strain to yield a preliminary determined velocity;
   second measuring at least a second parameter of the drilling fluid to yield at least a measured second parameter;
   adjusting the preliminary determined velocity based on the measured second parameter to yield an adjusted velocity; and
   determining a flow rate of the drilling fluid based on the adjusted velocity.

2. The method of claim 1, wherein the changing of the output includes heating the drilling fluid.

3. The method of claim 2, wherein the changing of the output includes turning on the heater.

4. The method of claim 1, wherein the changing of the output includes turning off the heater.

5. The method of claim 1, wherein the second parameter includes a speed of sound through the drilling fluid.

6. The method of claim 5, wherein the adjusting includes:
   determining approximate relative amounts of water and oil in the drilling fluid based on the speed of sound through the drilling fluid; and
   compensating for influence of the approximate relative amounts of water and oil on the preliminary determined velocity.

7. The method of claim 1, wherein the second parameter includes a hydrostatic head of drilling fluid in the wellbore.

8. The method of claim 7, wherein the adjusting includes:
determining the hydrostatic head of drilling fluid in the wellbore to yield a determined hydrostatic head; and
compensating for influence of the determined hydrostatic head on the preliminary determined velocity.

9. The method of claim 1, wherein the second parameter includes a hydrostatic head of fluid in the wellbore and a speed of sound through the drilling fluid.

10. The method of claim 9, wherein the adjusting includes:
determining the hydrostatic head of fluid in the wellbore to yield a determined hydrostatic head;
determining approximate relative amounts of water and oil in the drilling fluid based on the speed of sound through the drilling fluid; and
compensating for influence of the determined hydrostatic head on the preliminary determined velocity.

11. A system to measure fluid flow in a wellbore, the system comprising:
a probe including at least a heater;
a fiber optic cable connected to the probe; and
electronic computer hardware with software programmed to perform operations when the probe is lowered into a wellbore, the operations comprising:
changing an output of the heater to thereby change a temperature of drilling fluid moving over the fiber optic cable;
measuring a strain on the fiber optic cable caused by changing the temperature of the drilling fluid to yield a measured strain;
preliminarily determining a velocity of the drilling fluid from the measured strain to yield a preliminarily determined velocity;
measuring at least a second parameter of the drilling fluid to yield at least a measured second parameter;
adjusting the preliminary determined velocity based on the measured at least a second parameter to yield an adjusted velocity; and
determining a flow rate of the drilling fluid based on the adjusted velocity.

12. The system of claim 11, wherein the changing of the output includes heating the drilling fluid.

13. The system of claim 12, wherein the changing of the output includes turning on the heater.

14. The system of claim 11, wherein the changing of the output includes turning off the heater.

15. The system of claim 11, wherein the second parameter includes a speed of sound through the drilling fluid.

16. The system of claim 15, wherein the adjusting includes:
determining approximate relative amounts of water and oil in the drilling fluid from the speed of sound through the drilling fluid; and
compensating for influence of the approximate relative amounts of water and oil on the preliminary determined velocity.

17. The system of claim 11, wherein the second parameter includes a hydrostatic head of drilling fluid in the wellbore.

18. The system of claim 17, wherein the adjusting includes:
determining the hydrostatic head of drilling fluid in the wellbore to yield a determined hydrostatic head; and
compensating for influence of the determined hydrostatic head on the preliminary determined velocity.

19. The system of claim 11, wherein the second parameter includes a hydrostatic head of fluid in the wellbore and a speed of sound through the drilling fluid.

20. The system of claim 19, wherein the adjusting includes:
determining the hydrostatic head of fluid in the wellbore to yield a determined hydrostatic head;
determining approximate relative amounts of water and oil in the drilling fluid from the speed of sound through the drilling fluid; and
compensating for influence of the determined hydrostatic and the determined hydrostatic head on the preliminary determined velocity.

* * * * *